United States Patent
El-Moaty et al.

(10) Patent No.: US 11,806,363 B1
(45) Date of Patent: Nov. 7, 2023

(54) GREEN SYNTHESIS OF SILVER NANOPARTICLES USING EUPHORBIA DENDROIDES AQUEOUS EXTRACT

(71) Applicant: King Faisal University, Al-Ahsa (SA)

(72) Inventors: Heba Ibrahim Abd El-Moaty, Al-Ahsa (SA); Rasha Abu-Khudir, Al-Ahsa (SA); Mostafa M. H. Khalil, Al-Ahsa (SA); Nadia A. Soliman, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/123,630

(22) Filed: Mar. 20, 2023

(51) Int. Cl.
| | | |
|---|---|---|
| A61K 33/38 | (2006.01) | |
| A61K 36/47 | (2006.01) | |
| A61P 31/10 | (2006.01) | |
| A61P 3/04 | (2006.01) | |
| A61P 3/10 | (2006.01) | |
| A61P 35/00 | (2006.01) | |
| A61K 9/51 | (2006.01) | |
| A61P 31/04 | (2006.01) | |

(52) U.S. Cl.
CPC ............ *A61K 33/38* (2013.01); *A61K 9/5192* (2013.01); *A61K 36/47* (2013.01); *A61P 3/10* (2018.01); *A61P 31/04* (2018.01); *A61P 31/10* (2018.01); *A61P 35/00* (2018.01)

(58) Field of Classification Search
None
See application file for complete search history.

(56) References Cited

PUBLICATIONS

Ahmad,N., et al., Green Fabrication of Silver Nanoparticles using Euphorbia serpens Kunth Aqueous Extract, Their Characterization, and Investigation of Its In Vitro Antioxidative, Antimicrobial, Insecticidal, and Cytotoxic Activities, BioMed Research International, vol. 2022,11 Pgs.,Publ. Jan. 9, 2022. (Year: 2022).*
Abd El-Moaty et al., "Characterization and evaluation of multiple biological activities of phytosynthesized gold hanoparticles using aqueous extract of Euphorbia dendroides", Nanomaterials and Nanotechnology. 2022;12.
Ahmad et al., "Phyto-fabrication, purification, characterization, optimization and biological competence of nano-silver", Feb. 2021, IET Nanobiotechnology, 15(1).
Periyasami et al., "Biogenic Silver Nanoparticles Fabricated by Euphorbia granulata Forssk's Extract: Investigating the Antimicrobial, Radical Scavenging, and Catalytic Activities", Journal of Nanomaterials, vol. 2022, Article ID 3864758, 13 pages, 2022.
Nasrollahzadeh et al., "Euphorbia helioscopia Linn as a green source for synthesis of silver nanoparticles and their optical and catalytic properties", Jul. 2015, Journal of Colloid and Interface Science, 450.
Arif et al., "Green Synthesis of Silver Nanoparticles Using Euphorbia wallichii Leaf Extract: Its Antibacterial Action against Citrus Canker Causal Agent and Antioxidant Potential", Molecules 2022, 27(11), 3525.
Ahmad et al., "Green Fabrication of Silver Nanoparticles using Euphorbia serpens Kunth Aqueous Extract, Their Characterization, and Investigation of Its In Vitro Antioxidative, Antimicrobial, Insecticidal, and Cytotoxic Activities", Biomed Res Int. 2022; 2022: 5562849.
Phull et al., "Synthesis of Silver Nanoparticles using Euphorbia wallichii Extract and Assessment of their Bio-functionalities", Medicinal Chemistry, vol. 16, Issue 4, pp. 495-506, 2020.
Elumalai et al., "Green synthesis of silver nanoparticle using Euphorbia hirta L and their antifungal activities", Archives of Applied Science Research, 2010, 2 (6): 76-81.

* cited by examiner

*Primary Examiner* — Dominic Lazaro
(74) *Attorney, Agent, or Firm* — Nath, Goldberg & Meyer; Richard C. Litman

(57) ABSTRACT

*Euphorbia dendroides* silver nanoparticles can have a crystalline structure and an average particle size ranging from about 7 nm to about 13 nm. The *Euphorbia dendroides* silver nanoparticles may be synthesized by providing a *Euphorbia dendroides* extract and combining the *Euphorbia dendroides* extract with silver nitrate. The resultant *Euphorbia dendroides* silver nanoparticles may be useful in treating a variety of conditions including bacterial infections, diabetes, inflammation, and cancer.

20 Claims, 5 Drawing Sheets

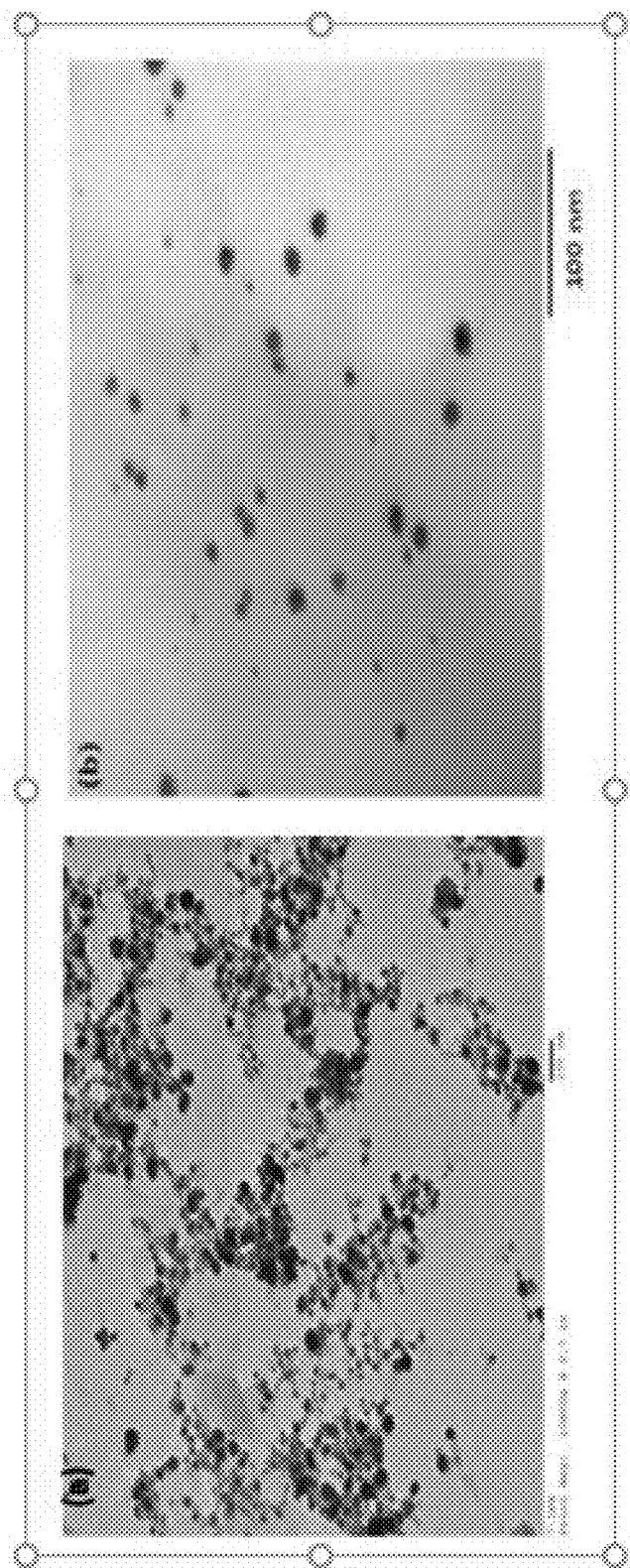
*FIG. 2A*  *FIG. 2B*

GREEN SYNTHESIS OF SILVER NANOPARTICLES USING EUPHORBIA DENDROIDES AQUEOUS EXTRACT

BACKGROUND

1. Field

The disclosure of the present patent application relates to silver nanoparticles, and particularly, to silver nanoparticles synthesized by bio-reduction of *Euphorbia dendroides* extract.

2. Description of the Related Art

Recently, nanoparticles have demonstrated important uses in a variety of fields. Nanoparticles have been used in electronics, sensing, optics, and medicine, for example.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used. Further, the therapeutic potential of plant extracts has been compromised due to the lack of controlled delivery of an effective dose to the desired target site.

Among plant genera, *Euphorbia* is widely distributed and more than 5% of *Euphorbia* species are utilized in traditional medicine to treat various diseases. *Euphorbia dendroides* is a plant belonging to the *Euphorbia* family. The plant has been used medically for its anti-proliferative, antioxidant, and anti-inflammatory properties, as well as other therapeutic properties, which may be attributed to the high content of polyphenols with diverse biological activities.

Thus, nanoparticles synthesized using an environmentally friendly method solving the aforementioned problems are desired.

SUMMARY

The present subject matter relates to *Euphorbia dendroides* silver nanoparticles (ED-AgNPs). The *Euphorbia dendroides* silver nanoparticles can have a spherical shape and a crystalline structure. In an embodiment, the *Euphorbia dendroides* nanoparticles can have an average particle size ranging from about 7 nm to about 13 nm.

In an embodiment, the present subject matter relates to a method of synthesizing *Euphorbia dendroides* silver nanoparticles, comprising: dissolving silver nitrate in deionized water to provide a silver solution; and adding an aqueous extract of *Euphorbia dendroides* to the silver solution to provide a mixture including *Euphorbia dendroides* silver nanoparticles.

According to an embodiment, the present subject matter relates to a method of inhibiting bacterial growth in a subject comprising administering an effective amount of the *Euphorbia dendroides* silver nanoparticles to a subject in need thereof.

According to an embodiment, the present subject matter relates to a method of treating diabetes in a subject comprising administering an effective amount of the *Euphorbia dendroides* silver nanoparticles to a subject in need thereof.

According to an embodiment, the present subject matter relates to a method of treating cancer in a subject comprising administering an effective amount of the *Euphorbia dendroides* silver nanoparticles to a subject in need thereof.

These and other features of the present subject matter will become readily apparent upon further review of the following specification and drawings.

BRIEF DESCRIPTION OF THE DRAWINGS

(FIG. 1B) fourier transform infrared (FTIR) spectrum of EDAE (*Euphorbia dendroides* aqueous extract), ED-AgNPs, and ED-AuNPs.

FIGS. 2A-2B depict transmission electron microscopy (TEM) images showing (FIG. 2A) the ED-AgNPs formed with spherical structures and homogenous distribution; and (FIG. 2B) ED-AuNPs formed with almost spherical structures.

Similar reference characters denote corresponding features consistently throughout the attached drawings.

DETAILED DESCRIPTION OF THE PREFERRED EMBODIMENTS

Figure 1A:
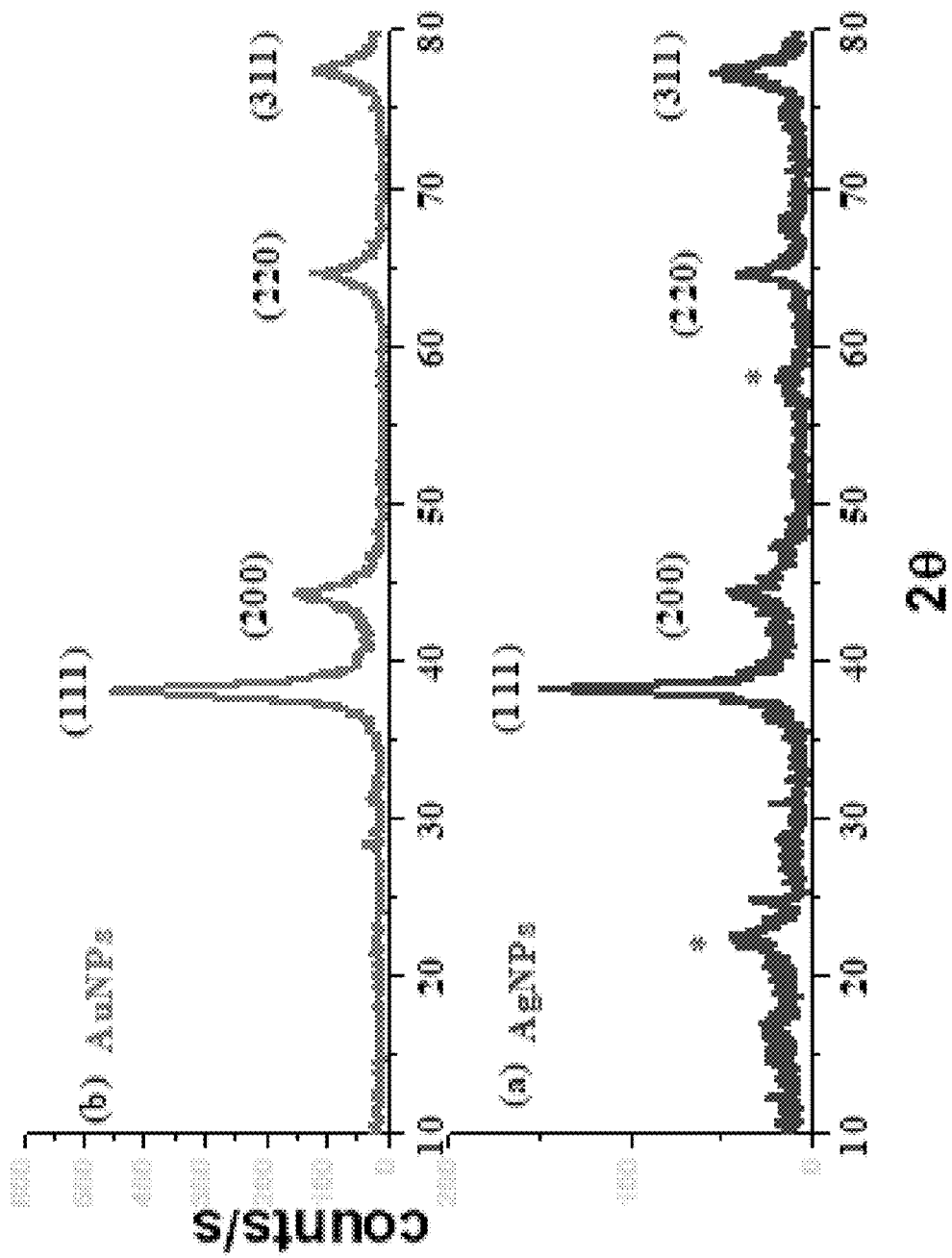
FIGS. 1A-1B depict (FIG. 1A) X-ray diffraction (XRD) analysis of ED-AgNPs and ED-AuNPs.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "patient" refers to any single subject for which treatment is desired. In certain embodiments, the patient herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In an embodiment, the present subject matter relates to *Euphorbia dendroides* silver nanoparticles (ED-AgNPs). The *Euphorbia dendroides* silver nanoparticles may be synthesized by dissolving silver nitrate in deionized water to provide a silver solution; and adding an aqueous extract of *Euphorbia dendroides* to the silver solution to provide a mixture including *Euphorbia dendroides* silver nanoparticles. In one embodiment, the aqueous extract comprises *Euphorbia dendroides* aerial parts. In an embodiment, 10 g of the *Euphorbia dendroides* aerial parts aqueous extract can be added to 1 ml silver nitrate solution, with the volume being adjusted to 10 ml with deionized water. In an embodiment, the bio-reduction process converts $Ag^+$ to $Ag^0$ nanoparticles as evidenced by the color change of the solution from yellow to brownish-yellow to deep brown. In an embodiment, the *Euphorbia dendroides* can contain flavanones, terpenoids and proteins.

In an embodiment, the silver solution is prepared by dissolving silver nitrate ($AgNO_3$) in 100 ml deionized boiling water in a dark bottle. pH of the silver solution can be monitored using sulfuric acid and sodium hydroxide.

In an embodiment, the *Euphorbia dendroides* silver nanoparticles can have a spherical shape and a crystalline structure. The *Euphorbia dendroides* silver nanoparticles can have an average particle size ranging from about 7 nm to about 13 nm, or about 10 nm. In other embodiments, the *Euphorbia dendroides* silver nanoparticles can have an average particle size of 7 nm, 8 nm, 9 nm, 10 nm, 11 nm, 12 nm, or 13 nm.

An embodiment of the present subject matter is directed to a pharmaceutical composition comprising the *Euphorbia dendroides* silver nanoparticles and a pharmaceutically acceptable carrier.

An embodiment of the present subject matter is directed to a method of making a pharmaceutical composition including mixing the *Euphorbia dendroides* silver nanoparticles with a pharmaceutically acceptable carrier. For example, the method of making a pharmaceutical composition can include mixing the *Euphorbia dendroides* silver nanoparticles under sterile conditions with a pharmaceutically acceptable carrier with preservatives, buffers, and/or propellants to create the pharmaceutical composition.

To prepare the pharmaceutical composition, the *Euphorbia dendroides* silver nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The *Euphorbia dendroides* silver nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the *Euphorbia dendroides* silver nanoparticles or an amount effective to treat a disease, such as a bacterial infection, may be determined initially from the Examples described herein and adjusted for specific targeted diseases using routine methods.

The *Euphorbia dendroides* silver nanoparticles can have antibacterial, anti-diabetic, anti-cancer, and anti-inflammatory properties. The *Euphorbia dendroides* silver nanoparticles can be administered to a subject in need thereof. In an embodiment, the *Euphorbia dendroides* silver nanoparticles can be administered to a subject in need thereof to inhibit bacterial growth. In an embodiment, the *Euphorbia dendroides* silver nanoparticles can be administered to a subject to inhibit the growth of *Helicobacter pylori*. In a further embodiment, the *Euphorbia dendroides* silver nanoparticles can be administered to a subject in need thereof to treat inflammation. In another embodiment, the *Euphorbia dendroides* silver nanoparticles can be administered to a subject in need thereof to treat diabetes. In still another embodiment, the *Euphorbia dendroides* silver nanoparticles can be administered to a subject in need thereof to treat cancer. In an embodiment, the *Euphorbia dendroides* can be administered to a subject in need thereof to treat liver cancer or colon cancer.

An embodiment of the present subject matter is directed to a method of inhibiting bacterial growth in a subject, comprising administering to a subject in need thereof a therapeutically effective amount of the pharmaceutical composition according to the present subject matter.

An embodiment of the present subject matter is directed to a method of treating inflammation in a subject, comprising administering to a subject in need thereof a therapeutically effective amount of the pharmaceutical composition according to the present subject matter.

An embodiment of the present subject matter is directed to a method of treating diabetes in a subject, comprising administering to a subject in need thereof a therapeutically effective amount of the pharmaceutical composition according to the present subject matter.

An embodiment of the present subject matter is directed to a method of treating cancer in a subject, comprising administering to a subject in need thereof a therapeutically effective amount of the pharmaceutical composition according to the present subject matter.

The *Euphorbia dendroides* silver nanoparticles or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

*Euphorbia dendroides* Silver Nanoparticles

Silver nitrate ($AgNO_3$; $1 \times 10^{-2}$ M) stock solution was prepared by dissolving 0.169 g in 100 ml de-ionized boiling water in dark bottle. pH was monitored using sulfuric acid and sodium hydroxide.

For the synthesis of the silver nanoparticles, 10 g of *Euphorbia dendroides* aerial parts aqueous extract was added to the 1 ml $AgNO_3$ ($1 \times 10^{-2}$ M) solution and the volume was adjusted to 10 ml with de-ionized water. The reduction process $Ag^+$ to $Ag^0$ nanoparticles was followed by the color change of the solution from yellow to brownish-yellow to deep brown depending on studied parameters such as the extract concentration, time, temperature and pH.

Figure 1B:
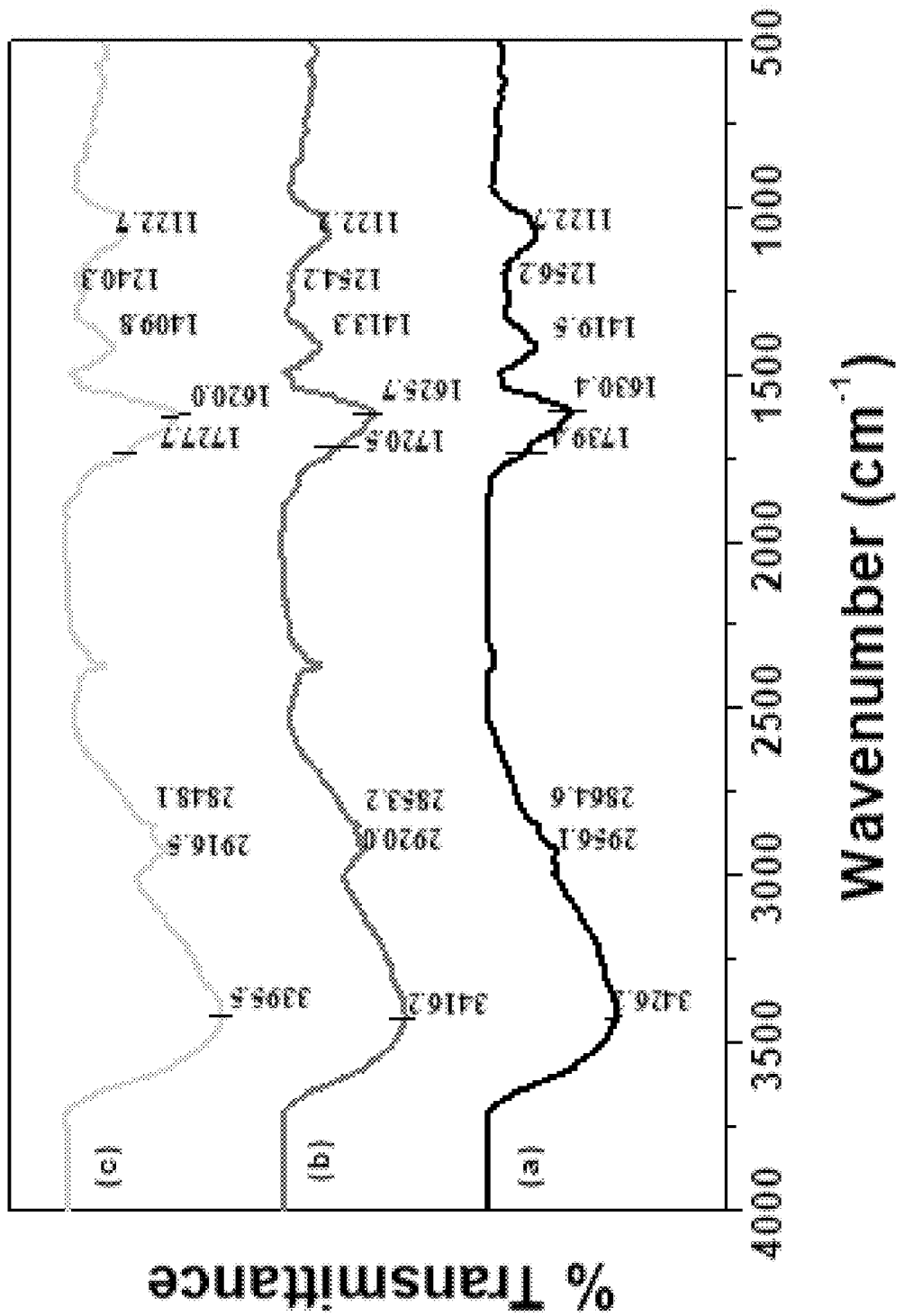

The ED-AgNPs were characterized and compared to *Euphorbia dendroides* gold nanoparticles (ED-AuNPs). FIGS. 1A-1B depict (FIG. 1A) X-ray diffraction (XRD) analysis of ED-AgNPs and ED-AuNPs; and (FIG. 1B) fourier transform infrared (FTIR) spectrum of EDAE (*Euphorbia dendroides* aqueous extract), ED-AgNPs, and ED-AuNPs. X-ray diffraction (XRD) patterns were obtained using a Shimadzu XRD-6000 diffractometer with Cu Ka ($\lambda=1.54056$ Å) to confirm the biosynthesis of nanoparticles. Fourier transform infrared (FTIR) spectra were recorded on a Nicolet 6700 FTIR spectrometer at room temperature.

The diffraction peaks for the ED-AgNPs in the XRD analysis were observed at 2θ values=38.17, 44.31, 64.44, and 77.34, which could be assigned to the 111, 200, 220, and 311 crystallographic planes, respectively. Hence, face center cubic (fcc) structure of the AuNPs synthesized using EDAE was confirmed. The Bragg's peak broadening in the XRD pattern distinctly indicates the formation of small-sized nanoparticles. There were some unidentified peaks appeared in the XRD pattern of ED-AgNPs with smaller intensity that might be due to crystalline bioorganic compounds from the extract.

Identification of the plausible biomolecules implicated in the formation, capping, and stabilization of biosynthesized NPs was carried out via FTIR analysis. FTIR spectrum of EDAE revealed peaks at 3426.6, 2959.1, 2853.3, 1739.4, and 1630 $cm^{-1}$. The strong peak located at 3426.6 $cm^{-1}$ is associated with O—H vibration in the biomolecules. The $CH_2$ anti-symmetric and symmetric stretching vibrations were observed at 2959.1 and 2853.3 $cm^{-1}$, respectively. The IR peak located at 1739.4 $cm^{-1}$ is assigned to the carbonyl (C=O) group, while the one at 1630 $cm^{-1}$ is assigned to amide I vibrations. The IR spectra of gold and silver nanoparticles exhibited narrower peaks shifted relative to the aqueous extract to 3395.5, 1620.1, 1727.7 $cm^{-1}$ and to 3416.21, 1625.76, 1720.54 $cm^{-1}$ for ED-AuNPs and ED-AgNPs, respectively. The presence of flavanones or terpenoids is indicated by the carbonyl, as they are adsorbed on the surface of metal nano-sized particles via interaction through the carbonyl groups in proteins and amino acids.

The size and morphology of the nanoparticles were examined and the TEM images were obtained on a JEOL-1200JEM. FIGS. 2A-2B depict transmission electron microscopy (TEM) images showing (FIG. 2A) the ED-AgNPs formed with spherical structures and homogenous distribution; and (FIG. 1B) ED-AuNPs formed with almost spherical structures. The scale bar corresponds to 100 nm.

The results obtained showed the formation of spherical and homogeneous distribution of ED-AgNPs and almost spherical ED-AuNPs with an average size of 10±3 and 15±3 nm, respectively.

Example 2

*Euphorbia dendroides* Silver Nanoparticles Activity

The antibacterial, anti-diabetic, and anti-cancer activities of the green-synthesized AgNPs (ED-AgNPs) were investigated.

Anti-Cancer Activity

The anticancer activity of the biosynthesized ED-AgNPs was assessed against the standard anticancer drug doxorubicin (DOX) and EDAE using the tetrazolium salt (3-(4,5-Dimethylthiazol-2-yl)-2,5-diphenyltetrazolium bromide, MTT). HepG2 and HCT-116 cells at a density of $10^4$ cells/well were seeded in 96-well plates and incubated for 24 h. The investigated ED-AgNPs, EDAE, and DOX were added at a final concentration (F.C.) ranging from 0-500 µg $mL^{-1}$ to the seeded cells for another 48 h at 37° C. and 5% $CO_2$. Subsequently, treated cells were incubated with MTT at 5 mg/mL F.C. for 4 h at 37° C. Finally, 100 µL DMSO were added to dissolve the water insoluble purple formazan crystals resulting from the reduction of MTT by viable cells. Using microplate reader, the cell viability was measured by recording absorbance (Abs) at 540 nm after 15 min (Tecan Infinite 200 Pro, Austria). A negative control of 10 µL of the MTT stock solution added to 100 µL of medium alone was included. Cell viability was reported relative to control, untreated cells (viability of which was set at 100%) as follows:

$$\text{Cell viability}(\%) = \frac{\text{Abs of treated cells}}{\text{Abs of control cells}} \times 100$$

Results were represented as mean values ±SD of three independent experiments.

The concentration required to inhibit 50% of cancer cell growth inn $mL^{-1}$ ($IC_{50}$) was estimated using GraphPad Prism 6 software package. All experiments were performed in triplicate and data were represented as mean values ±SD.

Table 1 shows in-vitro cytotoxic activities of DOX, ED-AuNPs, and *E. dendroides* aqueous extract (EDAE) against HepG2 and HCT-116 cell lines.

TABLE 1

| Cell line | DOX | ED-AgNPs | ED-AuNPs | EDAE |
| --- | --- | --- | --- | --- |
| HepG2 | 0.38 ± 0.07 | 6.2 ± 0.5 | 41.72 ± 1.26 | 55.26 ± 2.25 |
| HCT-116 | 0.86 ± 0.16 | 12 ± 1.2 | 44.96 ± 3.23 | 69.83 ± 0.96 |

Determination of $IC_{50}$ values (50% inhibition of cancer cell growth inn $mL^{-1}$) were performed in triplicate and expressed as mean values ±SD.

The results obtained pointed to the significant cytotoxic effect exerted by the photosynthesized silver nanoparticles (ED-AgNPs) compared to gold ones (ED-AuNPs) and the plant extract itself (EDAE).

Anti-Diabetic Activity

The potential anti-diabetic efficacy of crude *E. dendroides* aqueous extract (EDAE) and phytosynthesized AgNPs (ED-AgNPs) was assessed in vitro via determination of α-glucosidase inhibitory activity. The chromogenic substrate for alpha-D-glucosidase, p-nitrophenyl-α-D-glucopyranoside (pNPG), was used which was hydrolyzed to the yellow-colored product, p-nitrophenol, that can be detected at 405 nm using a microplate reader (BioTek Instruments, Inc., Winooski, VT). Calculation of the percentage inhibition (% Inhibition) of α-glucosidase activity was carried out using the formula:

$$\% \text{ Inhibition} = \frac{\text{Abs Control} - \text{Abs Sample}}{\text{Abs Control}} \times 100$$

The 50% inhibitory concentration ($IC_{50}$) was calculated using GraphPad Prism 6 software package. All experiments were performed in triplicate and data were represented as mean values ±SD.

Figure 4:
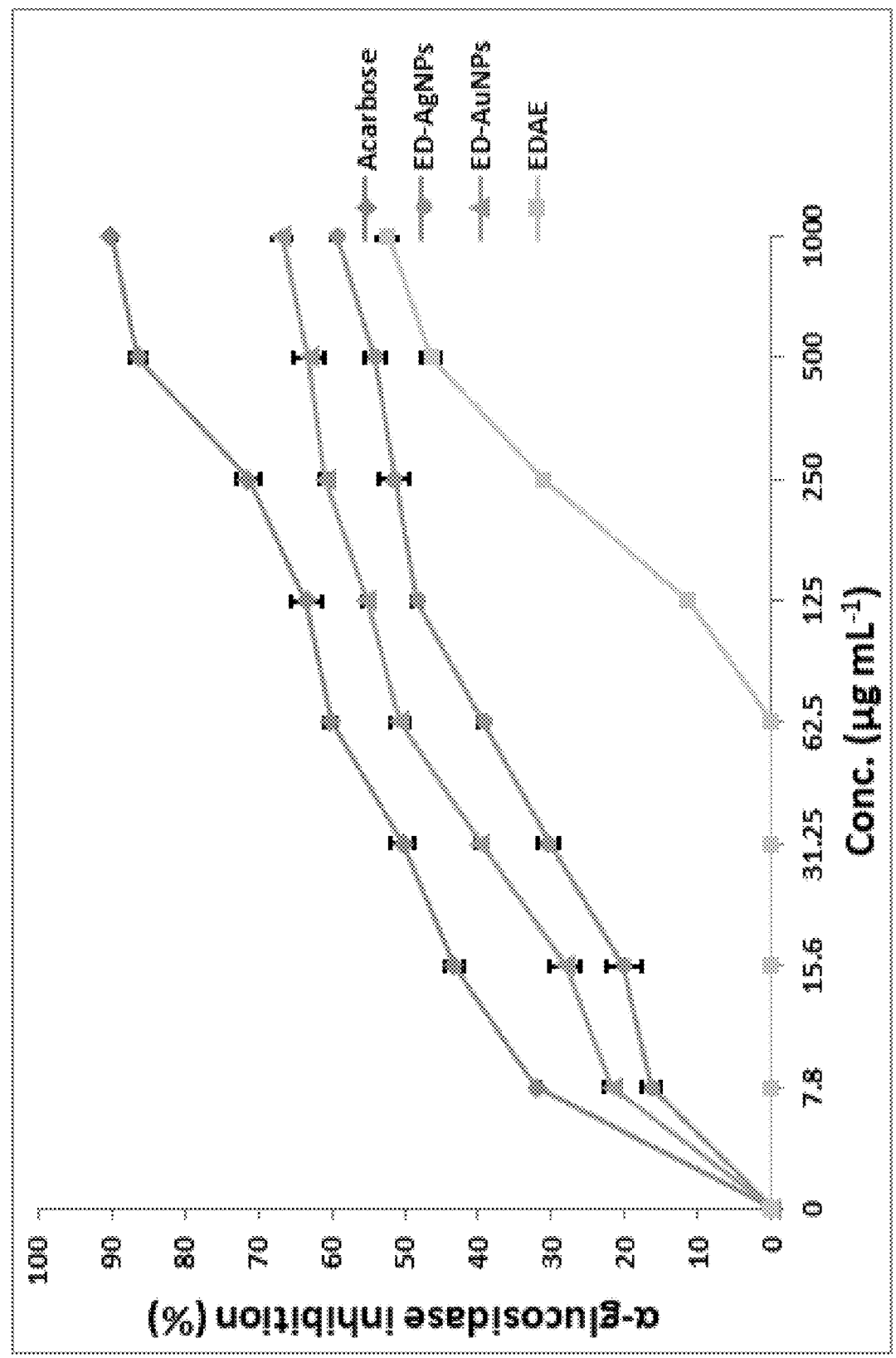
FIG. 4 is a comparative analysis of the anti-diabetic effect of the anti-diabetic drug, acarbose, ED-Ag-NPs, ED-AuNPs, and EDAE.

The anti-diabetic activity of ED-AgNPs and ED-AuNPs compared to EDAE was evaluated. As shown in FIG. 4, the biosynthesized ED-AgNPs and ED-AuNPs effectively inhibited intestinal α-glucosidase enzyme activity in a dose-dependent manner. The α-glucosidase inhibitory activity of ED-AuNPs exhibited the highest inhibitory activity (66.5% inhibition) when compared to ED-AgNPs (59.26% inhibition) and EDAE (52.34% inhibition) with $IC_{50}$ values of 19.8±1.97 µg $mL^{-1}$, 191.2 µg/mL and 214.67±10.88 µg $mL^{-1}$, respectively. The standard anti-diabetic drug acarbose has revealed the potent α-glucosidase inhibitory activity (90.1% enzyme inhibition) with an $IC_{50}$ value of 20.66±1.24 µg $mL^{-1}$. Hence, the results obtained pointed to the promising antidiabetic potential of the biosynthesized ED-AgNPs.

Anti-Bacterial Activity

The in vitro antibacterial efficacy of EDAE and ED-AgNPs against *H. pylori* was determined by the microwell dilution method as previously described with few modifications. For the determination of MIC in 96-well microtiter plate, serial two-fold dilutions of the examined samples in concentrations ranging from 125 to 0.24 µg $mL^{-1}$ with bacterial inoculum adjusted to 106 CFU/mL were used. As a reference, same concentrations of the standard antibiotic clarithromycin prepared in dimethyl sulfide (DMSO) were used. Each well of the 96-well microplate was filled with 40 µl of brain heart infusion (BHI) growth medium supplemented with 10% fetal bovine serum (FBS), 10 µl of bacterial inoculum, and 50 µl of the two-fold serially diluted tested samples. The plates were incubated at 37° C. for 72 h in 5% 02, 10% $CO_2$, and 85% $N_2$ atmosphere. Then, 40 µL of a freshly prepared (3-(4,5-Dimethylthiazol-2-yl)-2,5-diphenyltetrazolium bromide, MTT) solution at 0.5 mg $mL^{-1}$ final concentration was added to each well and incubated for a period of 30 min.

Minimal inhibitory concentrations (MIC) of the tested samples where no change in color of MTT is observed was recorded using an automatic reader at 620 nm. The percentage of inhibition was calculated using the formula:

$$\% \text{ Inhibition} = \frac{\text{Abs Control} - \text{Abs Sample}}{\text{Abs Control}} \times 100$$

Figure 3:
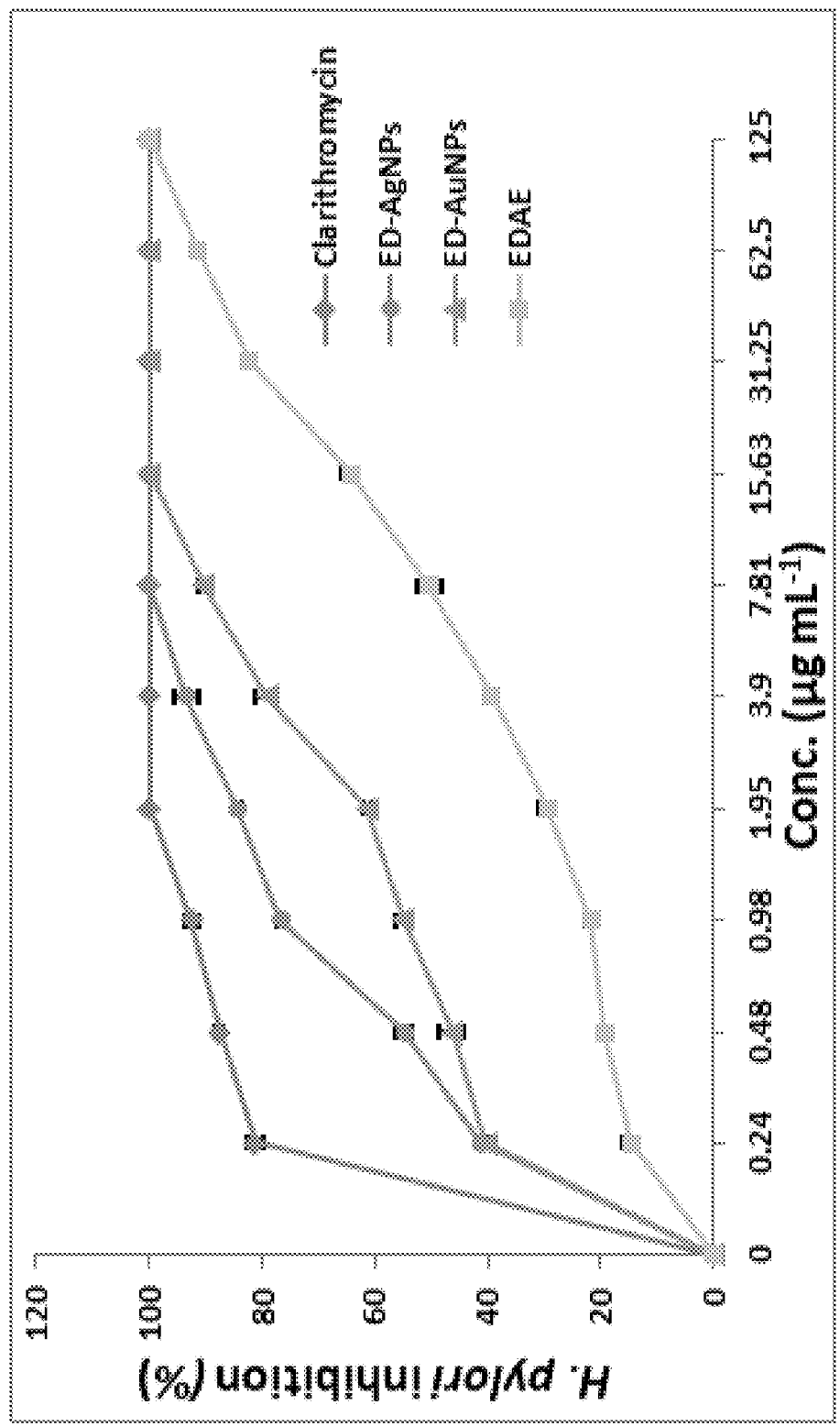
FIG. 3 is a comparative analysis of the anti-*Helicobacter pylori* effect of the antibiotic Clarithromycin, ED-AgNPs, ED-AuNPs, and EDAE.

The biosynthesized ED-AgNPs and ED-AuNPs as well as the aqueous extract of. *E. dendroides* (EDAE) were assessed for their anti-*H. Pylori* activity by the use of a micro-well dilution method and their minimum inhibitory concentrations (MICs) were compared to the standard drug, Clarithromycin, implied in anti-*H. Pylori* therapy. As shown in FIG. 3, when compared to EDAE and ED-AuNPs, ED-AgNPs exhibited a stronger bactericidal activity. The lower MICs besides the stronger antibacterial activities of ED-AgNPs (MIC=7.81 µg $mL^{-1}$) compared to ED-AuNPs (MIC=15.63 µg $mL^{-1}$) could be attributed to the smaller size of the silver nanoparticles. The lower MICs besides the stronger antibacterial activities of ED-AgNPs and ED-AuNPs compared to EDAE (MIC=125 µg $mL^{-1}$) could be attributed to the smaller size and the presence of the miller index in the cubic network of the former. Metal-based nanoparticles provide a significantly large surface area surrounding the bacterial effluent, which is anticipated to improve the extent of bacterial elimination.

Accordingly, it was determined that ED-AgNPs exhibited useful anticancer, antibacterial, and antidiabetic properties and could safely be used in several medical applications.

Example 3

Comparison Between the Photosynthesized Silver Nanoparticles from *Euphorbia* Dendroites (ED-AgNPs) and Those Prepared from Other *Euphorbia* Species The ED-AgNPs prepared and described herein were compared to silver nanoparticles formed using other *Euphorbia* species to show the unique and beneficial properties specific to the *Euphorbia* dendroites species. These comparisons are expressed below as follows.

Table 2 below relates to the synthesis of silver nanoparticles using *Euphorbia wallichii* extract and assessment of their biofunctionalities, as compared to the present silver nanoparticles using *Euphorbia* dendroites extract.

TABLE 2

| Point of Comparison | Silver NPs from *Euphorbia wallichii* | Silver NPs from *Euphorbia dendroites* |
|---|---|---|
| Extract/Plant part | Methanolic extract of roots | Aqueous extract of aerial parts |
| Size of nanoparticles | 63 ± 8 nm | 10 ± 3 nm |
| Reducing and Capping agents | phenolic (46.7 ± 2.4 µg GAE/mg) and flavonoid (11.7 ± 1.2 µg QE/mg) compounds | Flavanones, terpenoids and proteins |
| Antioxidant properties | √ | X |
| Antifungal properties | Against *A. fumigatus*, MIC 15 µg/disc | X |
| Antibacterial properties | Against *S. aureus*, MIC 3.33 µg/disc | Against *H. Pylori* MIC, 7.81 µg mL$^{-1}$ |
| Cytotoxicity (MTT assay) | LD50 0.3923 µg/ml (HeLa cells) | 6.2 ± 0.5 µg/mL (HepG-2) 12 ± 1.2 µg/mL (HCT-116) |
| Anti-diabetic | X | α-glucosidase inhibitory activity (191.2 µg/mL) |

Table 3 below relates to the synthesis of silver nanoparticles using *Euphorbia wallichii* leaf extract and assessment of their antibacterial action against citrus canker causal agent and antioxidant potential, as compared to the present silver nanoparticles using *Euphorbia* dendroites extract.

TABLE 3

| Point of Comparison | Silver NPs from *Euphorbia wallichii* | Silver NPs from *Euphorbia dendroites* |
|---|---|---|
| Extract/Plant part | Aqueous extract of leaves | Aqueous extract of aerial parts |
| Size of nanoparticles | 20 to 60 nm (average size of 24 nm) | 10 ± 3 nm |
| Reducing and Capping agents | Terpenoids, glycosides, tannins and flavonoids | Flavanones, terpenoids and proteins |
| Antioxidant properties (DPPH) | IC50 of 32 ug/mL | X |
| Antibacterial properties | Significant antibacterial activity against *X. axanopodis* | Against *H. Pylori* MIC, 7.81 µg mL$^{-1}$ |

Table 4 below relates to the synthesis of silver nanoparticles using *Euphorbia helioscopia* Linn and assessment of their optical and catalytic properties, as compared to the present silver nanoparticles using *Euphorbia* dendroites extract.

TABLE 4

| Point of Comparison | Ag NPs from *Euphorbia helioscopia* | Ag NPs from *Euphorbia dendroites* |
|---|---|---|
| Extract/Plant part | Aqueous extract of leaves | Aqueous extract of aerial parts |
| Size of nanoparticles | 2-14 nm | 10 ± 3 nm |
| Reducing and Capping agents | Polyphenolics | Flavanones, terpenoids and proteins |
| Antibacterial properties | X | Against *H. Pylori* MIC, 7.81 µg mL$^{-1}$ |
| Cytotoxicity (MTT assay) | X | 6.2 ± 0.5 µg/mL (HepG-2) 12 ± 1.2 µg/mL (HCT-116) |
| Anti-diabetic | X | α-glucosidase inhibitory activity (191.2 µg/mL) |
| Optical properties | √ | X |
| Catalytic activity | √ | X |

Table 5 below relates to the synthesis of silver nanoparticles using *Euphorbia hirta* L and assessment of their antifungal properties, as compared to the present silver nanoparticles using *Euphorbia* dendroites extract.

TABLE 5

| Point of Comparison | Ag NPs from *Euphorbia hirta* | Ag NPs from *Euphorbia dendroites* |
|---|---|---|
| Extract/Plant part | Ground leaves | Aqueous extract of aerial parts |
| Size of nanoparticles | 40-50 nm | 10 ± 3 nm |
| Reducing and Capping agents | ?????? | Flavanones, terpenoids and proteins |
| Antibacterial properties | X | Against *H. Pylori* MIC, 7.81 µg mL$^{-1}$ |
| Antifungal properties | Antifungal effect against *Candida albicans*, *C.kefyr*, *A.niger* | X |
| Cytotoxicity (MTT assay) | X | 6.2 ± 0.5 µg/mL (HepG-2) 12 ± 1.2 µg/mL (HCT-116) |
| Anti-diabetic | X | α-glucosidase inhibitory activity (191.2 µg/mL) |

Table 6 below relates to the synthesis of silver nanoparticles using *Euphorbia serpens* Kunth aqueous extract and assessment of their in vitro antioxidative, antimicrobial, insecticidal, and cytotoxic activities, as compared to the present silver nanoparticles using *Euphorbia* dendroites extract.

TABLE 6

| Point of Comparison | Ag NPs from *Euphorbia serpens* Kunth | Ag NPs from *Euphorbia dendroites* |
|---|---|---|
| Extract/Plant part | Aqueous extract of whole plant | Aqueous extract of aerial parts |
| Size of nanoparticles | 30-80 nm (average particle size = 50 nm) | 10 ± 3 nm |
| Reducing and Capping agents | Flavonoids, protein, tannins and saponins | Flavanones, terpenoids and proteins |
| Antibacterial properties | Antibacterial effect against *S. aureus*, *E. coli*, *P. aeruginosa*, and *S. typhi* | Against *H. Pylori* (MIC, 7.81 µg mL$^{-1}$) |
| Antifungal properties | No significant activity was shown | X |
| Antioxidant activity | Impressive antioxidant activity | X |

TABLE 6-continued

| Point of Comparison | Ag NPs from *Euphorbia serpens* Kunth | Ag NPs from *Euphorbia dendroites* |
|---|---|---|
| | compared to other metal nanoparticles | |
| Insecticidal Activity | √ | X |
| Cytotoxicity | Cytotoxic activity against *Artemia salina* with LD50 of 5.37-5.82 (brine shrimp bioassay) | 6.2 ± 0.5 µg/mL (HepG-2) 12 ± 1.2 µg/mL (HCT-116) |
| Anti-diabetic | X | α-glucosidase inhibitory activity (191.2 µg/mL) |

Table 7 below relates to the synthesis of silver nanoparticles using *Euphorbia granulata* Forssk's extract and assessment of their in vitro antimicrobial, radical scavening, and catalytic activities, as compared to the present silver nanoparticles using *Euphorbia* dendroites extract.

TABLE 7

| Point of Comparison | Ag NPs from *Euphorbia granulata* | Ag NPs from *Euphorbia dendroites* |
|---|---|---|
| Extract/Plant part | Aqueous extract of whole plant | Aqueous extract of aerial parts |
| Size of nanoparticles | 10.85 nm | 10 ± 3 nm |
| Reducing and Capping agents | Flavonoids, tannins, and phenolic compounds, glycoside, and proteins | Flavanones, terpenoids and proteins |
| Antibacterial properties | Antimicrobial effect against, *S. aureus, E. coli, L. monocytogenes, P. aeruginosa, K. pneumoniae,* and *E. faecalis* and two fungal pathogens (*C. albicans* and *Cryptococcus* sp.) (MIC = 6.24 – 100.0 µg/mL) | Against *H. Pylori* (MIC, 7.81 µg mL$^{-1}$) |
| Antioxidant activity (DPPH assay) | IC$_{50}$ 30.04 µg/mL | X |
| Catalytic activity | √ | X |

Collectively, the obtained data demonstrates the significant cytotoxic effects of the phytosynthesized silver nanoparticles from *Euphorbia* dendroites (ED-AgNPs) against certain common cancer types (hepatocellular and colon carcinoma) which have not been studied in other *Euphorbia* species. In addition, the antidiabetic effect of silver nanoparticles from any other *Euphorbia* species have not been previously assessed.

It is to be understood that the *Euphorbia dendroides* silver nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. *Euphorbia dendroides* silver nanoparticles comprising nanoparticles synthesized from *Euphorbia dendroides* extract and silver.

2. The *Euphorbia dendroides* silver nanoparticles of claim 1, wherein the nanoparticles have an average particle diameter of about 7 nm to about 13 nm.

3. The *Euphorbia dendroides* silver nanoparticles of claim 1, wherein the nanoparticles have an average particle diameter of about 10 nm.

4. A pharmaceutical composition, comprising the *Euphorbia dendroides* silver nanoparticles of claim 1 and a pharmaceutically acceptable carrier.

5. A method of inhibiting bacterial growth in a subject, comprising administering to a subject in need thereof a therapeutically effective amount of the pharmaceutical composition of claim 4.

6. The method of claim 5, wherein the pharmaceutical composition inhibits the growth of at least one bacteria that is *Helicobacter pylori*.

7. A method of treating inflammation in a subject, comprising administering to a subject in need thereof a therapeutically effective amount of the pharmaceutical composition of claim 4.

8. A method of treating diabetes in a subject, comprising administering to a subject in need thereof a therapeutically effective amount of the pharmaceutical composition of claim 4.

9. A method of treating cancer in a subject, comprising administering to a subject in need thereof a therapeutically, effective amount of the pharmaceutical composition of claim 4.

10. The method of claim 9, wherein the cancer is liver cancer or colon cancer.

11. A method of synthesizing *Euphorbia dendroides* silver nanoparticles, comprising:
dissolving silver nitrate in deionized water to provide a silver solution; and
adding an aqueous extract of *Euphorbia dendroides* to the silver solution to provide a mixture including *Euphorbia dendroides* silver nanoparticles.

12. The method of claim 11, further comprising heating the mixture.

13. *Euphorbia dendroides* silver nanoparticles prepared by the method of claim 11.

14. The *Euphorbia dendroides* silver nanoparticles of claim 13, wherein the nanoparticles have an average particle diameter of about 7 nm to about 13 nm.

15. The *Euphorbia dendroides* silver nanoparticles of claim 14, wherein the nanoparticles have an average particle diameter of about 10 nm.

16. A method of inhibiting bacterial growth in a subject, comprising administering to a subject in need thereof a therapeutically effective amount of the *Euphorbia dendroides* silver nanoparticles of claim 13.

17. The method of claim 16, wherein the pharmaceutical composition inhibits the growth of at least one bacteria that is *Helicobacter pylori*.

18. A method of treating diabetes in a subject, comprising administering to a subject in need thereof a therapeutically effective amount of the *Euphorbia dendroides* silver nanoparticles of claim 13.

19. A method of treating cancer in a subject, comprising administering to a subject in need thereof a therapeutically effective amount of the *Euphorbia dendroides* silver nanoparticles of claim 13.

20. The method of claim 19, wherein the cancer is liver cancer or colon cancer.

* * * * *

UNITED STATES PATENT AND TRADEMARK OFFICE
CERTIFICATE OF CORRECTION

| | |
|---|---|
| PATENT NO. | : 11,806,363 B1 |
| APPLICATION NO. | : 18/123630 |
| DATED | : November 7, 2023 |
| INVENTOR(S) | : Heba Ibrahim Abd El-Moaty et al. |

It is certified that error appears in the above-identified patent and that said Letters Patent is hereby corrected as shown below:

On the Title Page

Item (72):
Please remove Inventor 3 residence "Al-Ahsa (SA)" and replace with "Cairo (EG)".
Please remove Inventor 4 residence "Al-Ahsa (SA)" and replace with "Cairo (EG)".

Signed and Sealed this
Twenty-ninth Day of October, 2024

Katherine Kelly Vidal
*Director of the United States Patent and Trademark Office*